US00PP22394P2

(12) United States Plant Patent
Egger

(10) Patent No.: US PP22,394 P2
(45) Date of Patent: Dec. 20, 2011

(54) ***HEUCHERELLA* PLANT NAMED 'REDSTONE FALLS'**

(50) Latin Name: ***Heucherella* hybrid**
Varietal Denomination: Redstone Falls

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/806,089

(22) Filed: Aug. 4, 2010

(51) Int. Cl.
*A01H 5/00* (2006.01)

(52) U.S. Cl. ..... Plt./441

(58) Field of Classification Search ..... Plt./441
See application file for complete search history.

*Primary Examiner* — Susan McCormick Ewoldt
(74) *Attorney, Agent, or Firm* — Klarquist Sparkman, LLP

(57) ABSTRACT

A new and distinct *Heucherella* plant substantially as shown and described, characterized by its trailing habit, spring leaves of peachy orange with a slight white veil to summer and winter leaves of purple red to brown to olive green, a dark pattern on the veins, large palmately lobed leaves, and excellent vigor. *Heucherella* 'Redstone Falls' grows equally well in full sun or filtered shade in the Pacific Northwest.

1 Drawing Sheet

Botanical denomination: *Heucherella* hybrid.

Variety designation: 'Redstone Falls'.

Cross reference to: *Heucherella* 'Yellowstone Falls' (U.S. Plant patent application Ser. No. 12/806,079, applied for concurrently on Aug. 4, 2010).

The present invention relates to a new and distinct cultivar of *Heucherella* and given the cultivar name of 'Redstone Falls'. *Heucherella* is in the family Saxifragaceae. *Heucherella* 'Redstone Falls' originated from a controlled cross between *Heuchera* 909-2 (a proprietary unreleased *Heuchera villosa* hybrid), as the seed parent, and massed selected proprietary *Tiarella* trailing, as the pollen parent.

Compared to the seed parent *Heuchera* 909-2, the new cultivar is trailing with cream colored flowers rather than pink.

Compared to the trailing *Tiarella* parent, the new cultivar has peachy orange to rust red leaves rather than green.

Compared to its sibling, *Heucherella* 'Yellowstone Falls' (U.S. Plant patent application Ser. No. 12/806,079, applied for concurrently on Aug. 4, 2010), the new cultivar has purple red to brown to olive green foliage rather than yellow to lime.

This new *Heucherella* is unique in being the first trailing *Heucherella*. It is further characterized by:

1. spring leaves of peachy orange with a slight white veil to summer and winter leaves of purple red to brown to olive green,
2. a dark pattern on the veins,
3. large palmately lobed leaves,
4. growing equally well in full sun or filtered shade in the Pacific Northwest,
5. and excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a two-year-old *Heucherella* 'Redstone Falls' in bloom, growing in the ground in shade in the trial field in June in Canby, Oreg.

FIG. 2 shows the foliage color of the same plant in late summer.

DETAILED PLANT DESCRIPTION

The following is a detailed description of the new *Heucherella* cultivar based on observations of a two-year-old specimens growing in the ground in the garden and trial fields in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $5^{th}$ edition.

Plant:

*Form.*—Basal rosette and trailing, herbaceous perennial.
*Hardiness.*—USDA Zone 4 to 9.
*Size.*—18 cm tall from top of the foliage to the ground and 55 cm wide.
*Habit.*—Mounding and trailing.
*Vigor.*—Excellent.
*Roots.*—Fibrous, freely branching, fine, and white in color.

Stem:

*Size.*—6 mm wide and grows to 44 cm long.
*Internode length.*—3 cm usually.
*Stem color.*—Greyed Purple 187B.

Leaf:

*Type.*—Simple.
*Arrangement.*—Rosette and alternate.
*Shape.*—Ovate.

*Lobing/division.*—5 palmate lobes with the terminal the longest, each with shallow secondary lobes.

*Venation.*—Palmate.

*Margins.*—Crenate.

*Apex.*—Mucronulate.

*Base.*—Cordate.

*Blade size.*—Grows to 12 cm long and 10 cm wide.

*Surface texture.*—Glandular both surfaces.

*Petiole description.*—Grows to 19 cm long and 2 mm wide, glandular hairs, Greyed Purple N186D.

*Leaf color.*—Variable depending on temperature and light conditions; spring topside Greyed Red 178B to Greyed Orange 177B with a slight veil in between the veins. White N155A, and a dark pattern on the veins, Greyed Purple 187B, bottom side Greyed Purple 187D; summer and winter topside Greyed Red 178A to Greyed Orange 177A with a very slight veil White N155A, and a dark pattern on the veins, Greyed Purple 187B, bottom side closest to Greyed Purple 187D; mature leaves in shade or shaded are Yellow Green 147B tinted Greyed Orange 177A and with the dark pattern Greyed Purple 187B.

Inflorescence:

*Size.*—4.5 cm wide and 16 cm long.

*Type.*—Raceme.

*Number of flowers per raceme.*—About 60.

*Number of racemes.*—20.

*Peduncle.*—Grows to 20 cm tall, 3 mm wide at base, glandular hairs, Greyed Orange 176B.

*Pedicel.*—Grows to 8 mm long, with glandular hairs, Greyed Orange 177B.

*Bloom period.*—April to July in Canby, Oreg.

Flower bud:

*Size.*—1.5 mm wide and 2 mm long.

*Description.*—Glandular puberulent, ovoid.

*Color.*—White N155B with base Red Purple 63C.

Flower:

*Type.*—Perfect.

*Shape.*—Campanulate.

*Size.*—2 mm deep and 2 mm wide.

*Petal description.*—5 in number, oblanceolate, 2 mm long, reflexed, tip acuminate, base attenuate, margin entire, glabrous on both sides, White NN155D on both sides.

*Calyx description.*—5 mm deep and 4 mm wide, with 5 lobes, divided ¾ way to the base, campanulate, glandular hairs on outside, glabrous inside, tip obtuse, margin entire, White 155C with base Red Purple 63D.

*Stamen description.*—5 in number, filaments 2 mm long, White NN155D, anthers sterile, less than 1 mm, Greyed Orange 165A.

*Pistil description.*—One central two beaked pistil, 4 mm long, White 155B.

*Fragrance.*—None.

*Lastingness.*—Each raceme blooms for about 2 weeks on the plant.

Fruit and seed: None

Disease and pest tolerance: No known resistances. Excellent disease tolerance to powdery mildew. All *Heucherella* are susceptible to root weevils.

I claim:

1. A new and distinct *Heucherella* plant as herein illustrated and described.

* * * * *

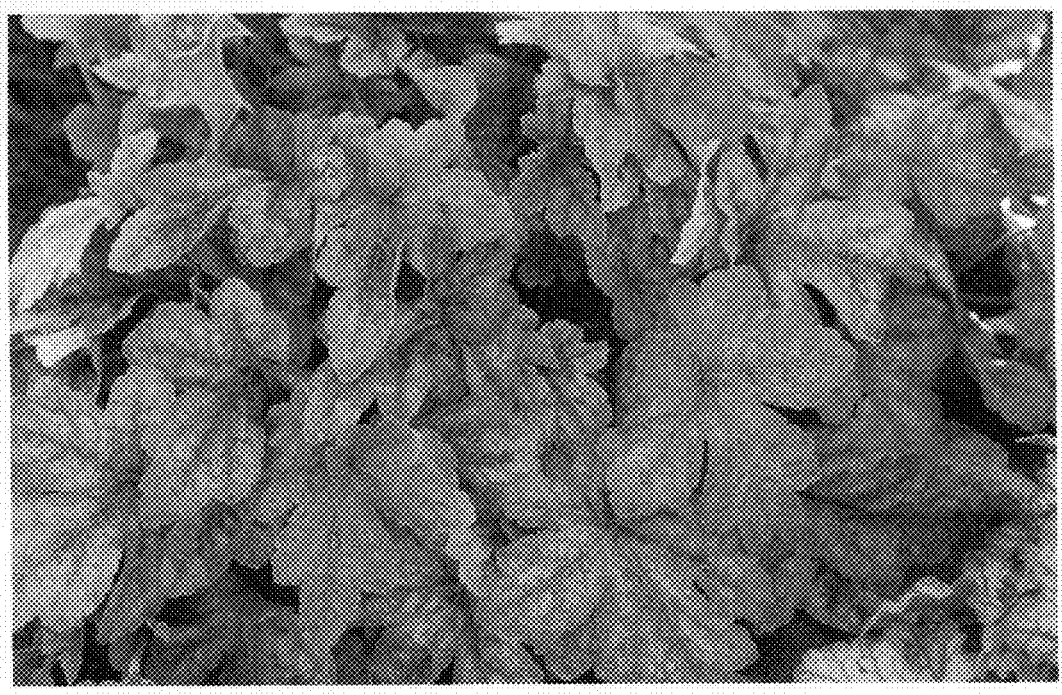

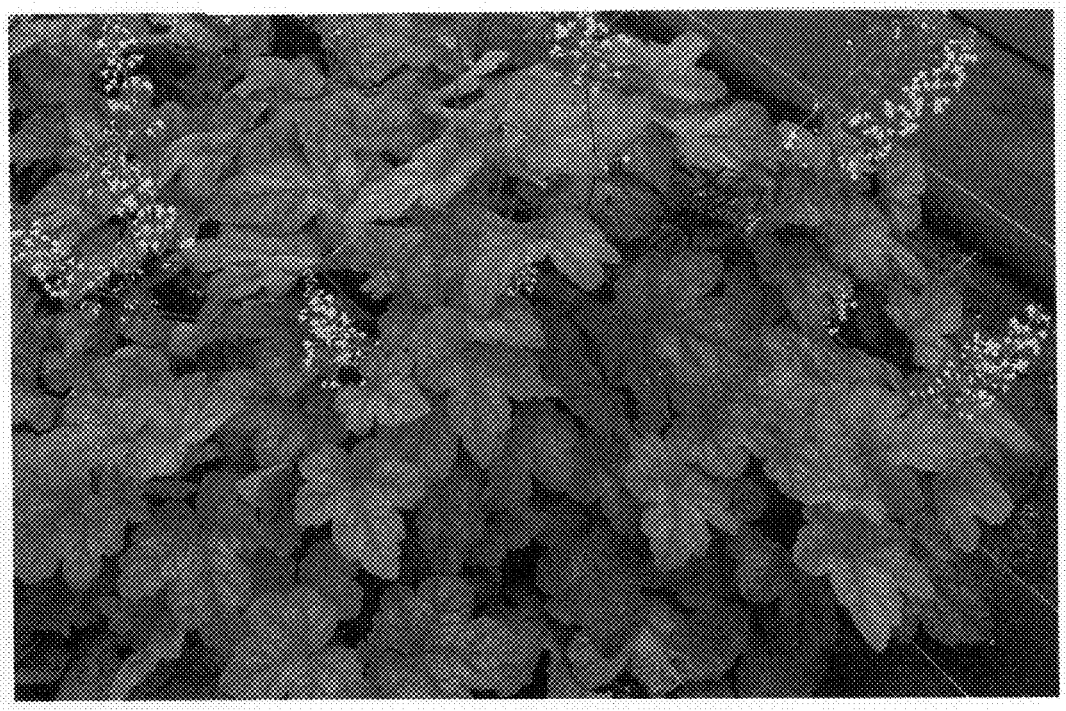
Figure 1 above, Figure 2 below